(12) United States Patent
Lloyd et al.

(10) Patent No.: US 10,363,427 B2
(45) Date of Patent: Jul. 30, 2019

(54) ELECTRICAL SAFETY SYSTEM

(71) Applicants: Michael Shane Lloyd, Atlanta, GA (US); Jonathan Jason Langberg, Atlanta, GA (US)

(72) Inventors: Michael Shane Lloyd, Atlanta, GA (US); Jonathan Jason Langberg, Atlanta, GA (US)

( * ) Notice: Subject to any disclaimer, the term of this patent is extended or adjusted under 35 U.S.C. 154(b) by 76 days.

(21) Appl. No.: 15/046,260

(22) Filed: Feb. 17, 2016

(65) Prior Publication Data

US 2016/0235996 A1 Aug. 18, 2016

Related U.S. Application Data

(60) Provisional application No. 62/176,381, filed on Feb. 17, 2015.

(51) Int. Cl.
| | |
|---|---|
| *A61N 1/39* | (2006.01) |
| *A61B 5/053* | (2006.01) |
| *G01R 27/16* | (2006.01) |
| *A61B 5/00* | (2006.01) |
| *G01R 31/44* | (2006.01) |

(Continued)

(52) U.S. Cl.
CPC ............ *A61N 1/3925* (2013.01); *A61B 5/053* (2013.01); *A61B 5/6823* (2013.01); *G01R 27/16* (2013.01); *G01R 31/44* (2013.01); *A61B 2505/01* (2013.01); *A61H 31/007* (2013.01); *A61H 2201/0173* (2013.01); *A61H 2201/10* (2013.01); *A61H 2201/5076* (2013.01);
(Continued)

(58) Field of Classification Search
CPC .. A61N 1/3925; A61N 1/3931; A61N 1/3987; A61B 5/6823; A61B 5/053; A61B 2505/01; G01R 27/16; G01R 31/025; A61H 2230/65; A61H 2201/5076; A61H 2201/10; A61H 2201/0173; A61H 31/007
See application file for complete search history.

(56) References Cited

U.S. PATENT DOCUMENTS

| | | | |
|---|---|---|---|
| 4,785,812 A | 11/1988 | Pihl et al. | |
| 6,668,192 B1 * | 12/2003 | Parker | A61N 1/39 600/522 |

(Continued)

FOREIGN PATENT DOCUMENTS

WO WO2011033456 3/2011

OTHER PUBLICATIONS

The PCT Search Report and Written Opinion dated May 16, 2016 for PCT application No. PCT/US16/18310, 8 pages.

(Continued)

*Primary Examiner* — Rex R Holmes
(74) *Attorney, Agent, or Firm* — Lee & Hayes, P.C.

(57) ABSTRACT

Technologies are disclosed herein for a low impedance detection system. The detection system includes an electrical insulation and an impedance measurement device. The impedance measurement device can be used to test the impedance of the system when the barrier is placed between the user of the barrier and a source of electrical power. In a defibrillation system, a rescuer can place the barrier over the patient. An electrical power source can deliver electrical shocks to the patient. The impedance measurement device can monitor impedances of the system across various frequencies to detect electrical conditions that might be harmful to the rescuer.

15 Claims, 8 Drawing Sheets

(51) Int. Cl.
*A61H 31/00* (2006.01)
*G01R 31/02* (2006.01)

(52) U.S. Cl.
CPC ........ *A61H 2230/65* (2013.01); *A61N 1/3931* (2013.01); *A61N 1/3987* (2013.01); *G01R 31/025* (2013.01)

(56) References Cited

U.S. PATENT DOCUMENTS

| | | |
|---|---|---|
| 7,567,837 B2 | 7/2009 | Weil et al. |
| 2010/0234908 A1 | 9/2010 | Didon |
| 2011/0184484 A1 | 7/2011 | Vaisnys et al. |
| 2013/0218218 A1 | 8/2013 | Chapman et al. |
| 2014/0148869 A1 | 5/2014 | Stickney et al. |
| 2016/0059023 A1* | 3/2016 | Freeman .............. A61N 1/3925 607/8 |
| 2017/0361121 A1* | 12/2017 | Liu ..................... A61N 1/3987 |

OTHER PUBLICATIONS

The Partial Supplementary Search Report dated Nov. 8, 2018 for European patent application No. 16752998.1, 10 pages.

* cited by examiner

ELECTRICAL SAFETY SYSTEM

CROSS REFERENCE TO RELATED APPLICATIONS

This application claims the benefit of U.S. Provisional patent application No. 62/176,381 filed Feb. 17, 2015 entitled "Defibrillator shield to facilitate hands-on defibrillation," which is incorporated herein by reference herein in its entirety.

BACKGROUND

Countless human endeavors require the use of electrical power to facilitate some function. In some instances, the potential for a human to be exposed to electrical power is low. Devices that use electrical power are typically designed to provide a fixed, semi-permanent barrier between the human and the, potentially dangerous, electrical power powering the device. For example, in order to access potentially harmful electrical power, home appliances often have outer casings that require some effort to open up and expose a human to potentially dangerous electrical power.

However, in some endeavors, having a fixed, semi-permanent barrier is impractical or impossible. For example, power line workers often work in the vicinity of high voltages. Because of the countless variations in the locations they may need to access and work on the power lines, installing fixed, semi-permanent barriers is often not feasible.

Another human endeavor in which the use of a fixed, semi-permanent barrier can be impractical is when using a defibrillator. A defibrillator is an electrical device that provides an electric shock to the heart. The electrical shock is designed to help re-establish a normal rhythm in the case of a dangerous arrhythmia, as in cardiac arrest. A defibrillator works by using a high-voltage (hundreds to thousands of volts) impulse passed through the heart muscle to electrically reset the heart rhythm. The total energy that is delivered to a patient receiving a defibrillator shock can range from 50 to 360 joules.

A typical external defibrillator uses two contact pads or paddles to cause current to flow through the heart. Typically, one pad or paddle is put above and to the left of the heart and the other pad or paddle is put slightly beneath and to the right. Another method involves placing one paddle on the front of the body and the other on the patient's back. In order for the electric current to flow properly, and to reduce the risk of skin burns, the electrodes have to be applied close enough together. They must also make good electrical contact with the skin, so a solid or liquid conducting gel is usually applied to the patient's chest first.

During cardiac arrest, it is advantageous to minimize any interruptions between chest compressions performed during cardiopulmonary resuscitation and the delivery of electrical shock from an external defibrillators. However, manual cardiopulmonary resuscitation is often interrupted for relatively long periods during the defibrillation process for fear of inadvertently shocking the health care provider. To ensure the safety to healthcare providers performing the compressions, rescuers try to not contact the patient during the period of each shock. This interruption to compressions can reduce the efficacy of the resuscitation.

The use of uninterrupted hands-on defibrillation has been proposed. One such method is the use of non-conductive barriers to insulate the health care provider from the risk of a shock. In a simulated or best-case scenario, insulated barriers can shield health care providers against an electrical impulse that could decrease hands-off time, and improve patient outcomes of cardiac resuscitation. However, in actual use, the circumstances are often less than optimal. There may be fluids, body movement, and other factors that may render the insulated shield ineffective. For example, during compression, the rescuer may be shifting their body, possibly moving the barrier or resulting in a body part of the rescuer unknowingly being placed in contact with the patient. Thus, uninterrupted hands-on defibrillation using conventional technologies can pose a safety risk to the rescuer.

It is with respect to these considerations and others that the disclosure made herein is provided.

SUMMARY

The technologies disclosed herein provide functionality for an electrical safety system. In some examples, the system includes an electrical insulation and an impedance detection and dielectric strength detection device. In examples, the system further includes a plurality of leads that connect the impedance measurement device to a plurality of impedance input locations. In some examples, at least one impedance input location is a top surface of the electrical insulation and a second impedance input location is a location on an electrical drain (patient or other location) that receives power from an electrical source.

In some examples, the system includes an electrical power source that provides a shock voltage to defibrillate a patient. In some examples, the electrical power source can deliver a monophasic waveform or a biphasic waveform, or both. In some examples, the electrical insulation includes a first electrical pad configured to route the shock voltage from the electrical power source to the heart of the patient. A second electrical pad can be placed on the patient and connected to the electrical power source to complete the circuit to allow current to flow through the chest and heart of the patient.

In some examples, the impedance measurement device measures impedance between the electrical insulation (or drape) and the patient. The impedance may be measured across a plurality of frequencies. If the measured impedance at one or more frequencies is below a threshold value, the impedance measurement device can provide an output. For example, the impedance measurement device can cause a green light emitting diode ("led") on the barrier to extinguish and energize a red led, indicating a possibly unsafe condition. In other examples, the impedance measurement device can activate an interlock, preventing the electrical power source from delivering a shocking voltage to the pads.

The above-described subject matter can be implemented, in whole or in part, as a computer-controlled apparatus, a computer-implemented process, a computing system, or as an article of manufacture such as a non-transitory computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
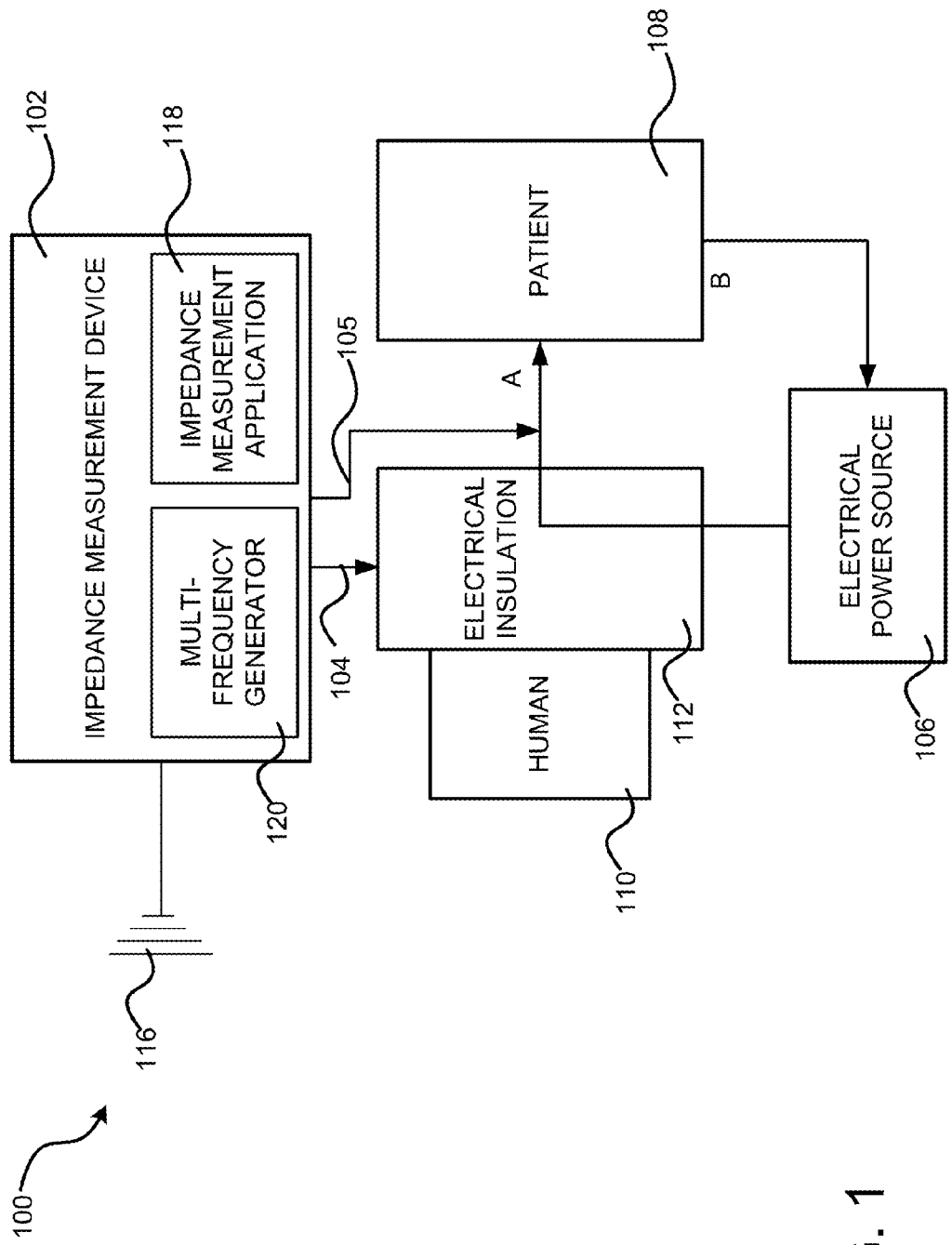
FIG. 1 is a block diagram showing aspects of an electrical safety system

The following detailed description is directed to technologies for an electrical safety system. While some aspects of the subject matter described herein are presented in the general context of program modules that execute in conjunction with the execution of an operating system and application programs on a computer system, those skilled in the art will recognize that other implementations can be performed in combination with other types of program modules.

Generally, program modules include routines, programs, components, data structures, and other types of structures that perform particular tasks or implement particular abstract data types. Moreover, those skilled in the art will appreciate that the subject matter described herein can be practiced with other computer system configurations, including handheld devices, multiprocessor systems, microprocessor-based or programmable consumer electronics, minicomputers, mainframe computers, and the like.

When working in the vicinity of electrical power, or on electrically energized devices, danger to a human may be present. In some instances, an electrical insulation may be used to attempt to shield (insulate) the human from the electrical power. For example, when using an electrical power source for defibrillation, an insulating flexible drape may be placed on the patient receiving the electrical shock treatment. The human rescuer may interact with the patient using the drape. For example, the rescuer may place the drape in a location that physically separates any body part of the rescuer from any body part of the patient. In some examples, the intent would be that when an electrical shock is delivered to the patient, the rescuer would be insulated from the voltage, and thus, not get shocked.

However, in real world situations, the environment in which the drape is used is often not static. For example, in the example provided above, when attempting to rescue a patient undergoing defibrillation, the patient and the rescuer often move about. There may be fluids, such as blood, vomit, or sweat, which change electrical characteristics of the rescue environment. In another example, workers on electrical equipment, such as high voltage power lines, often are in rainy or heated environments, causing the introduction of water that changes electrical characteristics of the worker's environment.

Thus, in some examples, it may be beneficial to actively measure and monitor the adequacy of the insulation separating a worker or rescuer from the source of high voltage.

In order to address this consideration, and potentially others, technologies are disclosed herein for providing information to a human (or another entity) regarding a leakage current pathway or an inadequate dielectric barrier that may pose an unsafe environment. In some examples, impedance between a surface in proximity to the worker/rescuer and the source of high voltage across a range of frequencies may be measured. The measured impedance across the range of frequencies may provide information that can be used in determining the dielectric strength of the barrier and therefore the risk of electrical shock in a particular environment. For example, in the defibrillation example, impedance measurements across a range of frequencies may help identify a potential for current leakage when an electrical shock is applied. In a defibrillation operation, it is desirable that the entire power generated by the electrical power source travel only through the patient's body. Current leakage caused by electrical short circuits or dielectric breakdown can reduce the efficacy of the defibrillating shock. Further, if the current leakage is through the rescuer, the rescuer may inadvertently, and undesirably, receive an electrical shock.

In the following detailed description, references are made to the accompanying drawings that form a part hereof, and which are shown by way of illustration specific embodiments or examples. It should be understood that while aspects of the presently disclosed subject matter are described in terms of use in a defibrillation system, the presently disclosed subject matter can be used in other applications, and are within the scope of the presently disclosed subject matter. Referring now to the drawings, aspects of a defibrillation system will be described.

FIG. 1 is a block diagram showing aspects of an electrical safety system 100 in a defibrillation operation. The electrical safety system 100 includes an impedance measurement device 102, an electrical insulation 112, and an electrical power source 106. In some examples, the electrical power source 106 generates and applies an electrical shock to a patient 108. In some examples, the electrical power source 106 delivers the electrical shock at locations A and B of the patient 108.

To help rescue the patient 108, a human 110 may attempt to perform chest compressions on the patient 108. To provide some degree of insulation between the human 110 and the patient 108, an electrical insulation 112 may be used. The electrical insulation 112 may have insulative and size properties that are designed to provide some degree of insulation between the human 110 and the patient 108. The electrical insulation 112 may be constructed of various materials, including, but not limited to, rubber, plastic, glass, and the like.

In some examples, it may be beneficial or desirable to measure impedance between various points of the electrical safety system 100. In some examples, the impedance measurement device 102 may be used. The impedance measurement device 102 may be powered using various electrical power sources. In some examples, the impedance measurement device 102 may be powered using a battery 116. In other examples (not illustrated), the impedance measurement device 102 may be powered using an external power source, such as the electrical power source 106 or power provided by the defibrillator unit. The presently disclosed subject matter is not limited to any particular configuration.

To measure impedance, the impedance measurement device 102 may have stored in memory instructions for an impedance measurement application 118. The impedance measurement application 118 may have instructions for energizing a multi-frequency generator 120. The multi-frequency generator 120 supplies electrical power at various frequencies. In some examples, the range of frequencies may include frequencies from ~0 Hz to 500 kHz. The presently disclosed subject matter is not limited to any particular frequencies or range of frequencies. The impedance of various aspects of the electrical safety system 100 is measured using leads 104 and 105. In FIG. 1, lead 104 is connected to the electrical insulation 112 and lead 105 is connected to the defibrillating electrode in contact with the patient 108. It should be noted that the presently disclosed subject matter is not limited to any particular number of leads or locations of attachment of the leads, as various locations may be measured. Various aspects of the impedance measurement device 102 can be performed using the ADuCM350 chipset from ANALOG DEVICES, INC. out of Norwood, Mass.

In some examples, the impedance measurement may be designed to determine the impedance that may put the human 110 at risk for receiving a hazardous amount of electrical current flow. For example, the electrical insulation 112 in contact with the patient 108 may have a theoretical or expected impedance profile across a range of frequencies for a given dielectric strength. The impedance measurement application 118 may be configured to receive the input from the lead 104 and lead 105. The impedance may be determined using techniques known by those of ordinary skill in the relevant art.

In some examples, if the measured impedance is different than an expected impedance profile, the impedance measurement application 118 may cause the generation of an output. In some examples, the output may be to change lighting in the electrical safety system 100 that indicates the possibility of an unsafe condition or an electrical short. In other examples, the output may be to prevent the application of the electrical power from the electrical power source 106 until the out-of-range impedance condition is cleared. The presently disclosed subject matter is not limited to any particular output.

During use, the human 110 may place the electrical insulation 112 over the patient 108. The human 110 may attach the electrical power source 106 to the patient 108 at locations A and B of the patient 108. The human 110 may attach the leads 104 and 105 from the impedance measurement device 102, or the leads 104 and 105 may be preinstalled. The human 110 may energize the impedance measurement device 102 and the electrical power source 106.

The human 110 may also perform chest compressions on the patient 108. In some examples, by using the electrical insulation 112, the human 110 may be able to continue applying compressions while the electrical power source 106 delivers electrical shocks to the patient 108. The impedance measurement device 102 will continually measure impedance during the "hands-on CPR" operation.

If the human 110 comes in direct contact with the patient 108, or sweat or other fluids make an electrical circuit between the human 110 and the patient 108, or various other instances, the impedance measurement device 102 may detect a low impedance, or out of range, condition. The low impedance condition may, in some examples, signal a condition in which the human 110 may inadvertently receive an electrical shock from the electrical power source 106. The low impedance condition may also indicate other issues. For example, the patient 108 may be covered in fluids that present a lower path to ground, causing the electrical shock to not fully move through the patient 108 (i.e. stray currents). An out of range impedance measurement may also indicate a condition where the insulating barrier through cracking or some other damage, may have inadequate dielectric strength to withstand a defibrillating shock.

Figure 2:
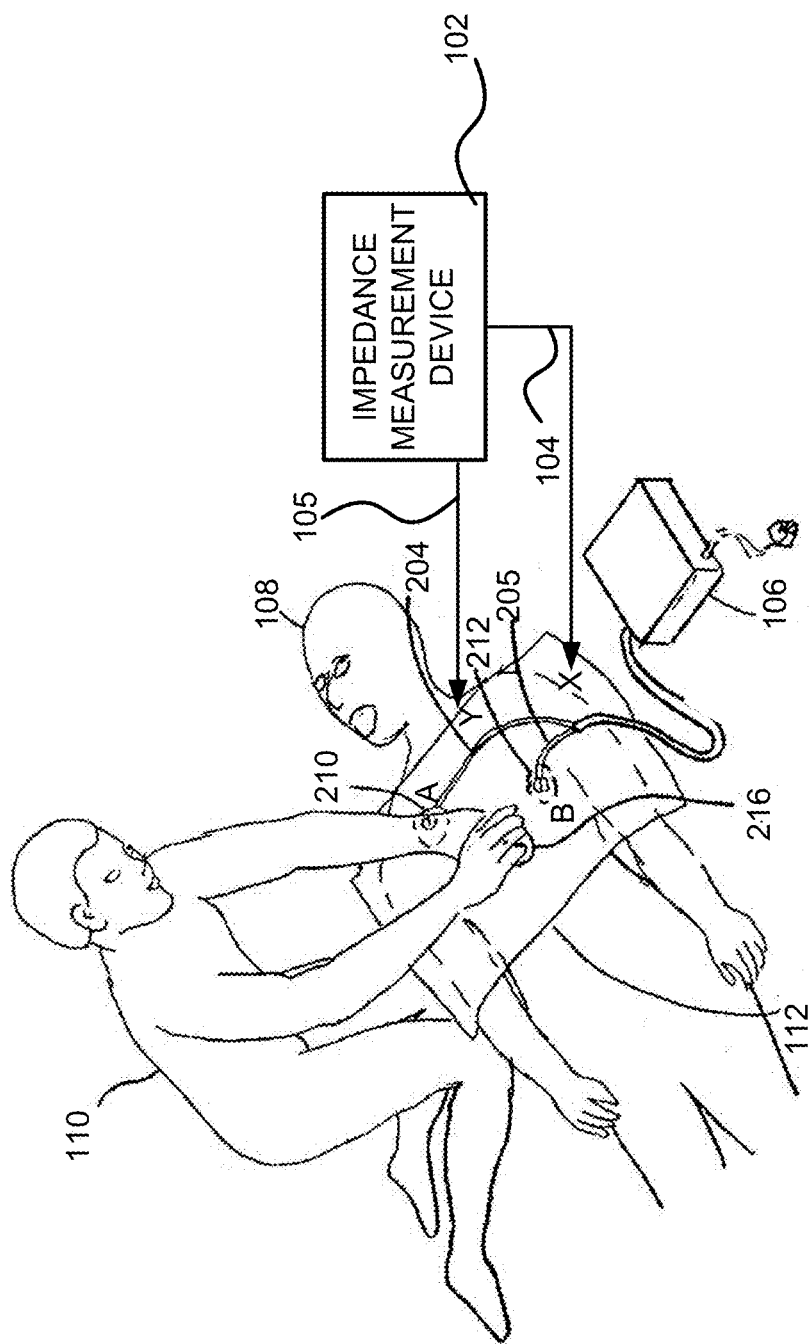
FIG. 2 is a diagram showing an electrical safety system in use.

FIG. 2 is a diagram showing the electrical safety system 100 in use. As illustrated, the human 110 has applied the electrical insulation 112 across a portion of the patient 108. The electrical power source 106 provides electrical shocks to the patient 108 through a first power cable 204 and a second power cable 205. The first power cable 204 is applied to the patient 108 at location A through pad 210. The second power cable 205 is applied to the patient 108 at location B through pad 212.

In some examples, location A is at or near a proximate location to the heart of the patient 108. In some examples, location B is at or near the side or back of the patient 108.

As illustrated in FIG. 2, the impedance measurement device 102 is connected to the electrical insulation 112 at location X via lead 104 and location Y via lead 105. In operation, the human 110 may give chest compressions at location 216 while the electrical power source 106 applies shock voltage to the patient 108. In some examples, the electrical insulation 112 insulates, either partially or wholly, the human 110 from the electrical shocks. In some examples, the impedance measurement device 102 continually measures the impedance between the electrical insulation 112 and the patient 108 or the human 110 at various frequencies. If an out-of-range impedance profile is detected, the impedance measurement device 102 may provide an indication or stop the electrical shocks as an output.

Figure 3:
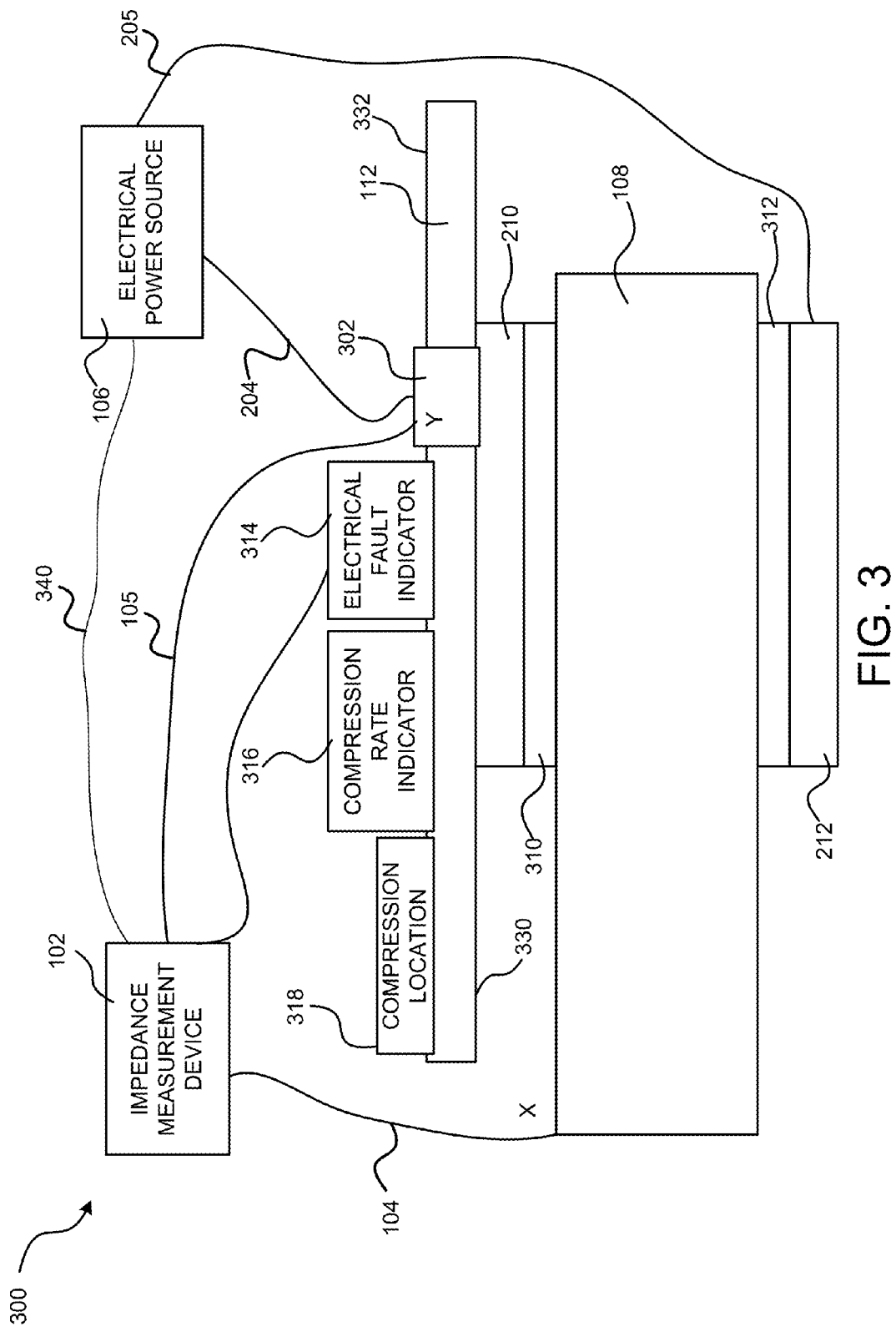
FIG. 3 is a side view of an electrical safety system.

FIG. 3 is a side view of a defibrillation system 300. The defibrillation system 300 includes the impedance measurement device 102 and the electrical power source 106. The electrical power source 106 applies shock voltage to the patient 108 via pad 210 through the first power cable 204 and a connector 302. The connector 302 connects the electrical power received from the electrical power source 106 through the electrical insulation 112. The electrical power source 106 also applies defibrillating voltage to the patient 108 through the second power cable 205 and the pad 212. In some examples, to help temporarily couple the pad 210 to the patient 108, a conductive gel 310 may be used. In a similar manner, to help temporarily couple the pad 212 to the patient 108, a conductive gel 312 may be used. In some configurations, the pad 210 is disposed proximate to an inner surface 330 of the electrical insulation 112 and is electrically isolated from an outer surface 332 of the electrical insulation 112 where a human rescuer can apply chest compressions.

During use, the human 110 may apply chest compressions to the patient 108 at location 318. If the impedance measurement device 102 detects an out-of-range impedance condition, the impedance measurement device 102 may output an electrical fault indication to an electrical fault indicator 314. The electrical fault indictor 314 can be lights, sounds, and the like. As discussed above, the output may also be a signal that prevents or stops the application of the defibrillating shock. In some examples, the impedance measurement device 102 may transmit a signal to the electrical power source 106 through connector 340. The electrical power source 106 may receive the signal as an input and stop the application of the electrical shocks. In some examples, the electrical insulation 112 may also include a compression rate indicator 316. The compression rate indicator 316 may be a light, sound, and the like that provides an input to the human 110 of a desired or recommended rate of chest compressions. The rate of compressions may be a predetermined or optimal rate that helps guide the human 110.

Figure 4:
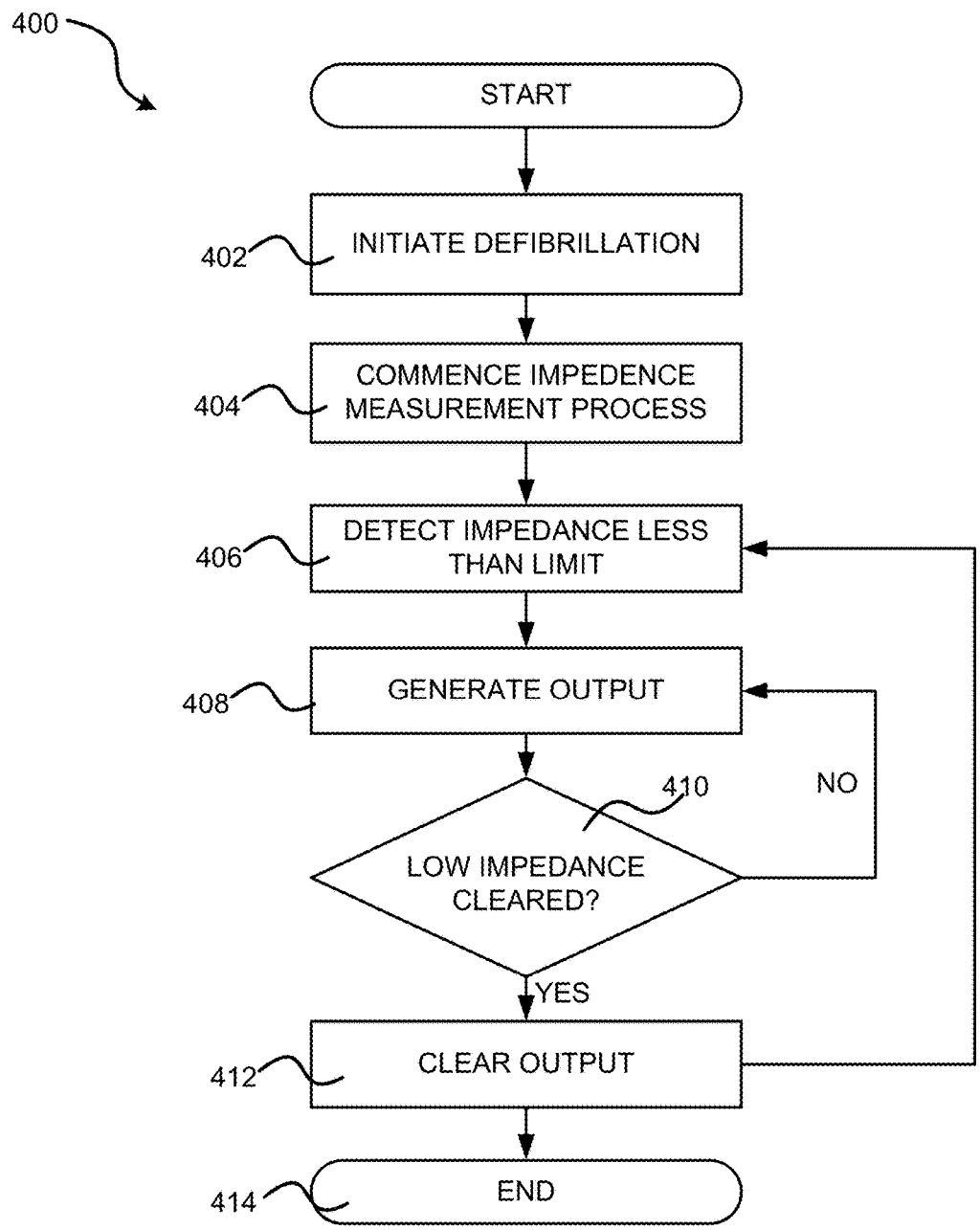
FIG. 4 is a flow diagram illustrating aspects of a routine disclosed herein for using an electrical safety system.

FIG. 4 is a flow diagram illustrating aspects of a routine 400 disclosed herein for the operation of the electrical safety system 100 in a defibrillation operation. It should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance requirements of the computing system. Accordingly, the logical operations described herein are referred to variously as operations, structural devices, acts, or modules. These operations, structural devices, acts and modules can be implemented in software, in firmware, in special purpose digital logic, and any combination.

The routine 400 begins at operation 402, where cardiopulmonary resuscitation (CPR) is initiated. As part of the CPR operation, the human 110 will place the electrical insulation 112 (drape) from the electrical safety system 100 over an area of the patient 108 that the human 110 may come into contact with. The electrical safety system 100 can also include the electrical power source 106. The human 110 can place the electrical insulation 112 over the patient 108 in a manner so that a pad under an underside surface of the electrical insulation 112 comes into contact with the patient 108. The human 110 can also place another pad on another location on the patient 108.

The human 110 can also energize an impedance measurement device. The impedance measurement device can include two leads that may be pre-installed on locations of the electrical insulation or other components of the electrical safety system 100. The human 110 can then energize the electrical power source and the impedance measurement device. The human 110 may also commence chest compressions.

Figure 5:
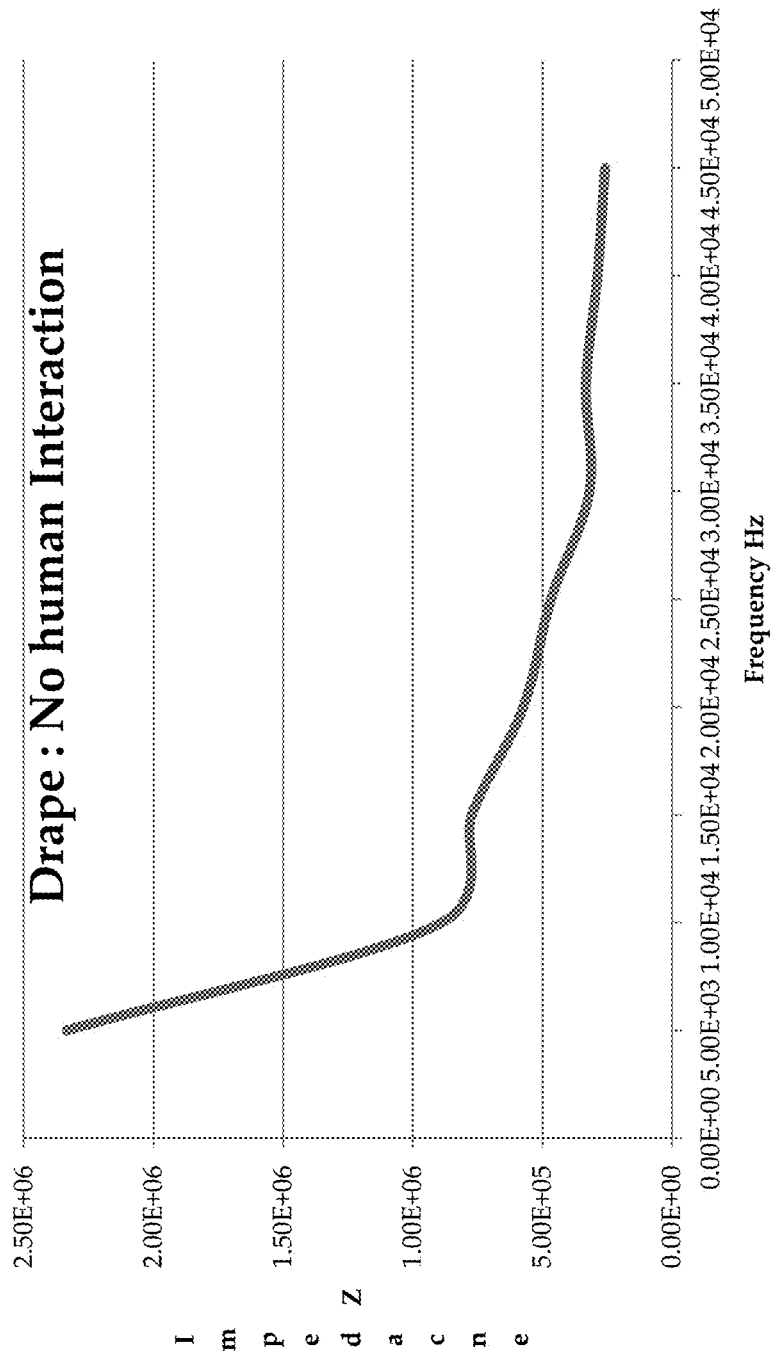
FIGS. 5-7 are graphs showing impedance measurements.

The routine continues to operation 404, where the impedance measurement device 102 measures impedance across various frequencies. The measurement of impedance across various frequencies can detect possible stray current conditions, inadequate dielectric strength of electrical insulation 112 or electrical shorts. For example, FIG. 5 is a graphical illustration of impedance characteristics of a drape placed over the patient without the human 110 touching the electrical insulation 112. As shown, at low frequencies, the electrical insulation 118 has high impedance characteristics, while at higher frequencies, the impedance decreases.

Figure 6:
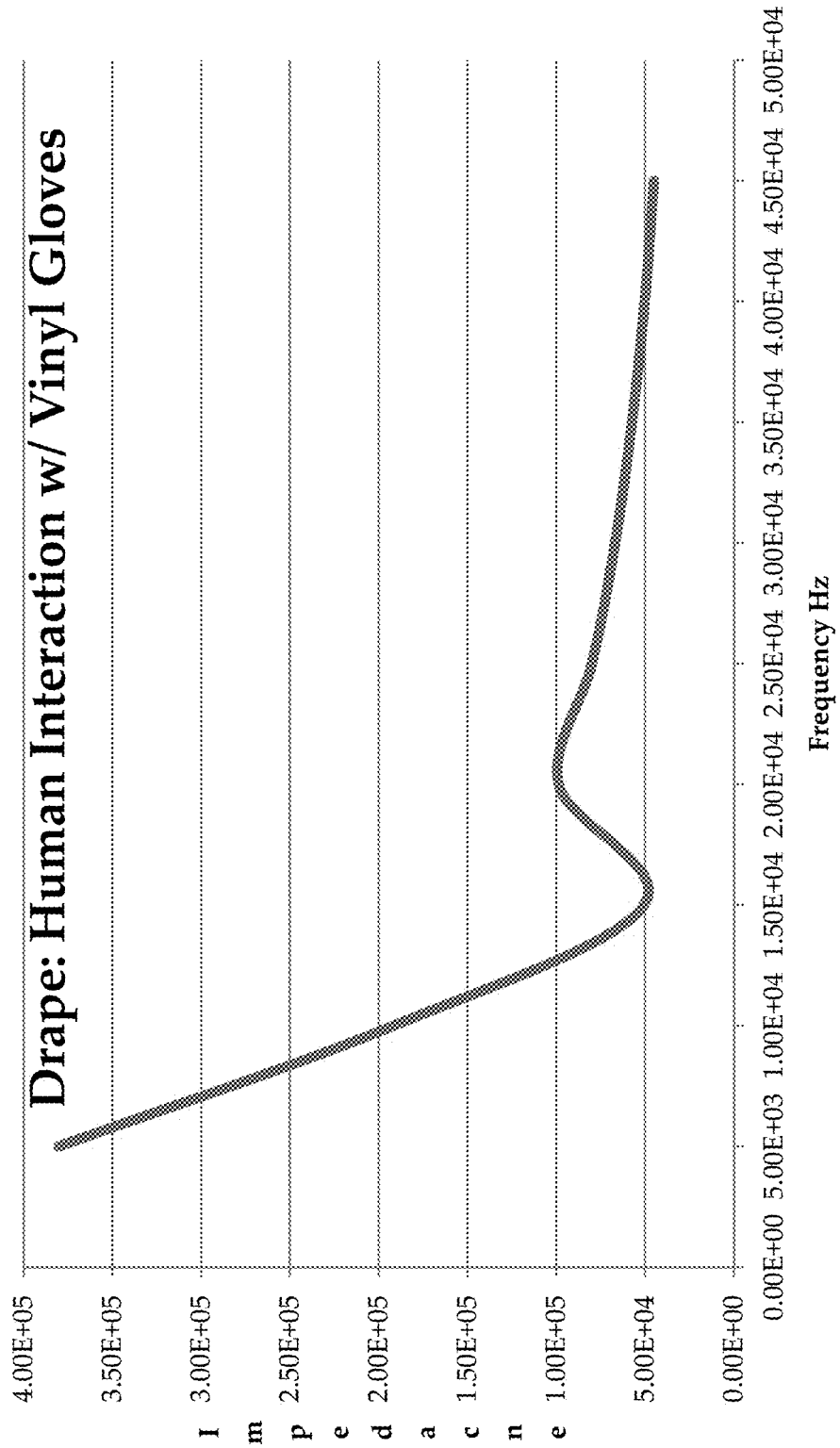

In FIG. 6, the impedance measurement device 102 was used to measure impedance when a human 110 is using gloves. As illustrated, around 15 kHz, impedance drops, showing an impedance characteristic that is different than that illustrated in FIG. 5. The drop in impedance may be a result of capacitive coupling between the hands of the human 110 and the conductive gel 310 or other factors.

Figure 7:
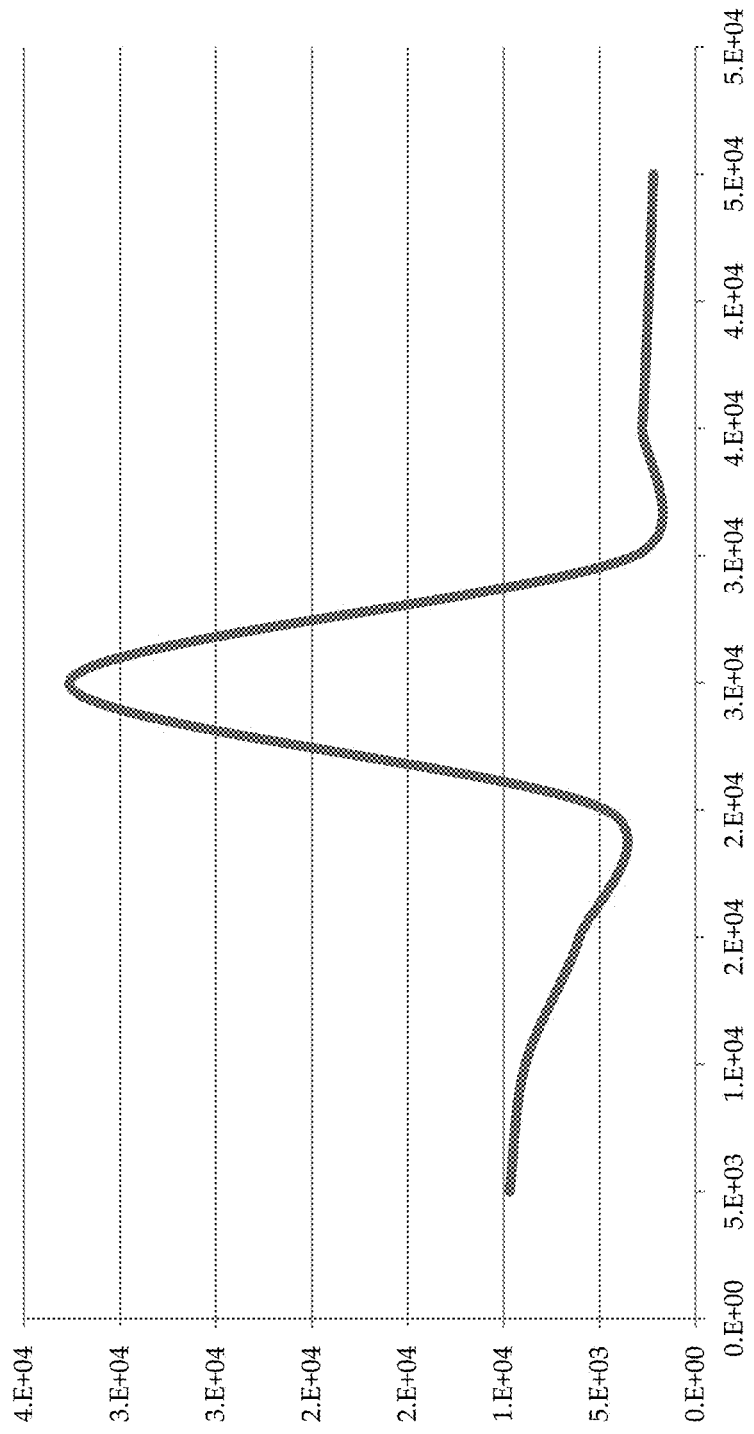

In FIG. 7, the impedance was measured at various frequencies between a gloved hand used by the human 110 and the pad 212. As shown, the impedance across most frequencies is generally lower than the barrier shown in FIG. 5. In some examples, the gloves will likely be thinner than the electrical insulation 112. So, if the materials are the same or similar, the impedance of glove to skin contact would be generally less across the various frequencies than the impedance of the barrier to skin contact.

Returning to FIG. 4, the routine 400 continues to operation 406, where the impedance measurement device 102 detects a low, or out of range, impedance condition. The low impedance condition may be measured across various surfaces. A low impedance condition may indicate the possibility of an electrical short or a condition of low dielectric strength that may allow stray current when an electrical shock is applied.

The routine 400 continues to operation 408, where the impedance measurement device 102 generates an output. As discussed above, the output may be lights, sounds, or a signal that prevents the application of an electrical shock to the patient. In some configurations, the output is designed to provide an indication to the human 110 to notify the human 110 of a potentially unsafe condition. In some examples, the electrical insulation 112 may have lights or other indicators in one or more places of the electrical insulation 112 that indicates where the low impedance condition is possibly existing.

The routine 400 continues to operation 410, where a determination is made as to whether or not the low impedance condition is cleared. If the low impedance condition has not cleared, the routine 400 continues to operation 408, where the output is maintained. If the low impedance condition has cleared, the routine 400 continues to operation 412, where the output, or indicator, is cleared. The routine 400 may thereafter end or continue from operation 412 back to operation 406 if CPR is continuing.

Figure 8:
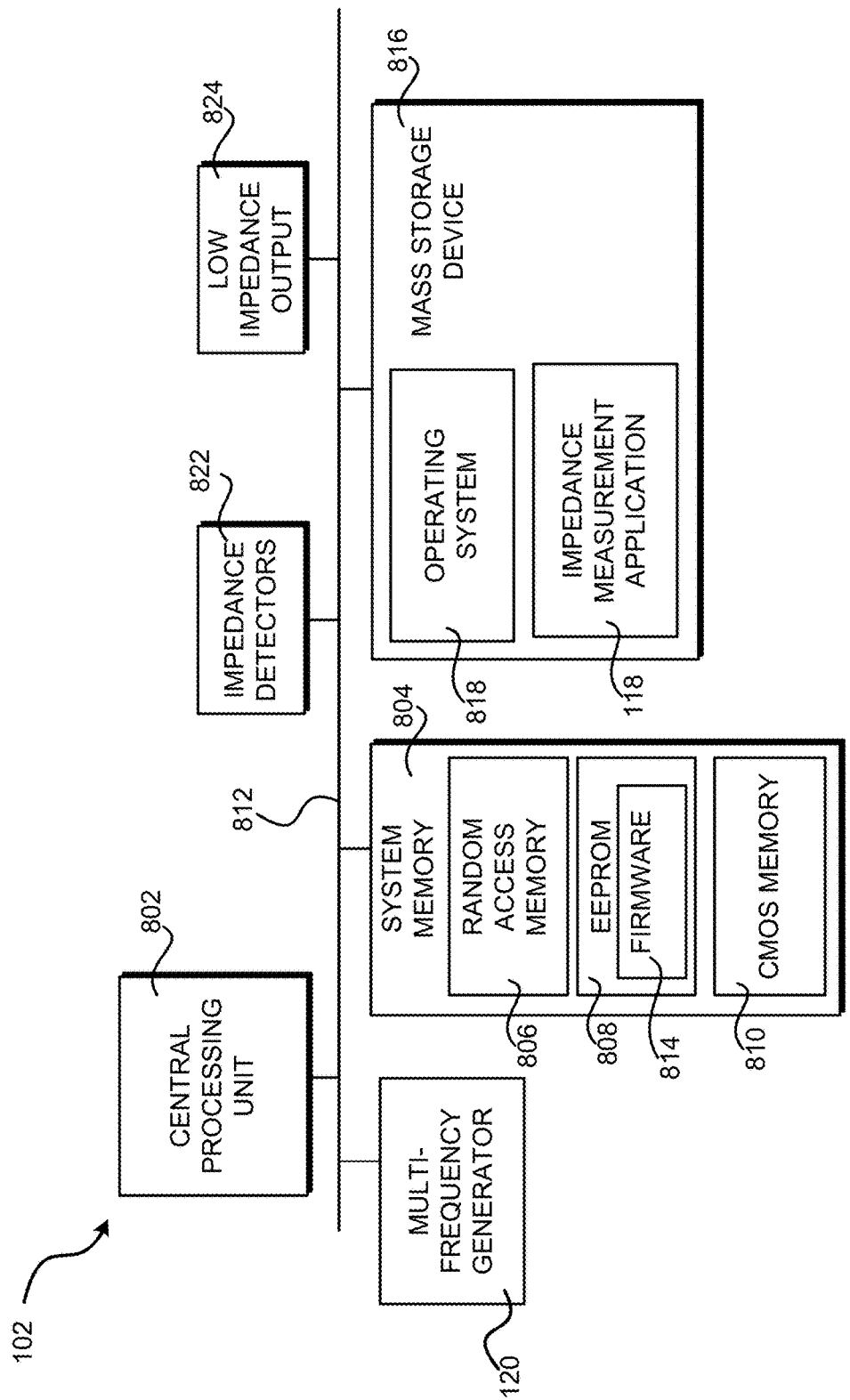
FIG. 8 is a computer architecture diagram showing a computer architecture suitable for implementing the various computer systems described herein.

Referring now to FIG. 8, an illustrative computer architecture for an impedance measurement device 102 utilized in the various embodiments of the disclosed subject matter will be described. The computer architecture shown in FIG. 8 includes a CPU 802, a system memory 804 that includes a RAM 806, an EEPROM 808, a CMOS memory 810, and a system bus 812 that couples the system memory 804 to the CPU 802. The impedance measurement device 102 can also include the multi-frequency generator 120. The EEPROM 808 may store firmware 814 for use in operating the impedance measurement device 102, such as a BIOS or an extensible firmware interface ("EFI"), containing the basic routines that help to transfer information between elements within the computer, such as during startup. The CMOS memory 810 is a battery-backed memory device that is used by the firmware 814 to store setting information for the impedance measurement device 102. Additional details regarding the architecture and operation of the firmware 814 will be provided below. It should be understood that in some implementations, such as software on a chip ("SoC"), various software, such as the impedance measurement application 118, may be part of the firmware.

The impedance measurement device 102 further includes a mass storage device 816 for storing an operating system 818 and the impedance measurement application 118, as well as other program modules (not illustrated). The mass storage device 816 is connected to the CPU 802 through a mass storage controller (not shown) connected to the system bus 812. The mass storage device 816 and its associated computer-readable media, provide non-volatile storage for the impedance measurement device 102. Although the description of computer-readable media contained herein refers to a mass storage device, such as a hard disk or CD-ROM drive, it should be appreciated by those skilled in the art that computer-readable media can be any available media that can be accessed by the impedance measurement device 102.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the impedance measurement device 102. The computer storage medium does not include non-transitory signals or non-transitory media.

The impedance measurement device includes impedance detectors 822. The impedance detectors 822 generate test voltages at various frequencies and receive the input from those test voltages. The input from the test voltages is used an input to the impedance measurement application 118. The impedance measurement application, when a low impedance condition is detected, can cause the impedance measurement device 102 to generate a low impedance output 824. The low impedance output 824 can be an indicator such as a light, speaker, and the like.

Based on the foregoing, it should be appreciated that technologies for an electrical safety system have been provided herein. Although the subject matter presented herein has been described in language specific to computer structural features, methodological acts, and computer readable media, it is to be understood that the invention defined in the appended claims is not necessarily limited to the specific features, acts, or media described herein. Rather, the specific features, acts and mediums are disclosed as example forms of implementing the claims.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A computer-implemented method, comprising:
measuring impedance between a rescuer and a patient while the rescuer is performing a hands-on CPR operation while a defibrillation system delivers one or more electrical shocks to the patient, wherein the defibrillation system comprises;
an electrical insulation configured to drape over at least a portion of the patient and placed between the rescuer and the patient;
a first pad in electrical communication with a power source through a first power cable to deliver an electrical shock to the patient, the first pad in electrical communication with the patient,
a second pad in electrical communication with the power source through a second power cable to deliver the electrical shock to the patient, the second pad in electrical communication with the patient; and
the power source to apply a shock voltage to the patient;
detecting a low impedance condition between the rescuer and the patient while the rescuer is performing the hands-on CPR operation; and
activating an indicator in response to detecting the low impedance condition.

2. The computer-implemented method of claim 1, further comprising determining if the low impedance condition has cleared.

3. The computer-implemented method of claim 2, wherein in response to determining that the low impedance condition has cleared, clearing the indicator.

4. The computer-implemented method of claim 1, wherein commencing measuring impedance comprises transmitting a test voltage at a plurality of frequencies.

5. The computer-implemented method of claim 1, wherein the indicator is a light or sound.

6. The computer-implemented method of claim 1, wherein the indicator is an electrical signal to an electrical power source to prevent delivery of an electrical shock to the patient.

7. An apparatus, comprising:
at least one processor; and
a computer-readable storage medium having instructions stored thereupon that are executable by the processor and which, when executed by the processor, cause the apparatus to:
measure impedance between a rescuer and a patient while the rescuer is performing a hands-on CPR operation while a defibrillation system delivers one or more electrical shocks to the patient, wherein the defibrillation system comprises;
an electrical insulation configured to drape over at least a portion of the patient and placed between the rescuer and the patient;
a first pad in electrical communication with a power source through a first power cable to deliver an electrical shock to the patient, the first pad in electrical communication with the patient,
a second pad in electrical communication with the power source through a second power cable to deliver the electrical shock to the patient, the second pad in electrical communication with the patient; and
the power source to apply a shock voltage to the patient; and
activate an indicator in response to detecting the low impedance condition.

8. The apparatus of claim 7, wherein the computer-readable storage medium further comprises instructions to determine if the low impedance condition has cleared.

9. The apparatus of claim 8, wherein the computer-readable storage medium comprises further instructions to clear the indicator in response to a determination that the low impedance condition has cleared.

10. The apparatus of claim 7, wherein the computer-readable storage medium comprises further instructions to transmit a test voltage at a plurality of frequencies to commence impedance measurements.

11. The apparatus of claim 7, wherein the indicator is a light or sound.

12. The apparatus of claim 7, wherein the indicator is an electrical signal to an electrical power source to prevent delivery of an electrical shock to the patient.

13. The computer-implemented method of claim 1, wherein measuring impedance between the rescuer and the patient comprises measuring an impedance between an impedance input location at a top surface of the electrical insulation and a second impedance input location on the patient.

14. The computer-implemented method of claim 4, further comprising:
determining that a measured impedance at one or more frequencies is below a threshold value; and
providing an output to activate the indicator.

15. The computer-implemented method of claim 14, further comprising providing the output to activate an interlock to prevent the power source from applying the shock voltage.

* * * * *